United States Patent [19]
Disel

[11] Patent Number: 5,669,769
[45] Date of Patent: Sep. 23, 1997

[54] ILLUMINATION AND CONNECTOR DENTAL HANDPIECE ASSEMBLY

[75] Inventor: Jimmy D. Disel, San Jose, Calif.

[73] Assignee: Aerotech Dental Systems, Inc., Sunnyvale, Calif.

[21] Appl. No.: 642,842

[22] Filed: May 3, 1996

Related U.S. Application Data

[62] Division of PCT/US94/12520, Nov. 3, 1994 which is a continuation-in-part of Ser. No. 147,750, Nov. 4, 1993, Pat. No. 5,476,379.

[51] Int. Cl.$^6$ .................................................. A61C 3/00
[52] U.S. Cl. .................................................. 433/29; 433/98
[58] Field of Search ........................... 433/29, 98, 99, 433/101

[56] References Cited

U.S. PATENT DOCUMENTS

| | | | |
|---|---|---|---|
| 4,171,572 | 10/1979 | Nash | 32/27 |
| 4,208,579 | 6/1980 | Scrivo et al. | 250/227 |
| 4,303,392 | 12/1981 | Rollofson | 433/126 |
| 4,330,274 | 5/1982 | Friedman et al. | 433/29 |
| 4,334,863 | 6/1982 | Magid et al. | 433/29 |
| 4,403,957 | 9/1983 | Mossle et al. | 433/29 |
| 4,477,252 | 10/1984 | Lieb et al. | 433/29 |
| 4,902,225 | 2/1990 | Lohn | 433/80 |
| 5,033,960 | 7/1991 | Heil | 433/29 |
| 5,074,785 | 12/1991 | Malata, Jr. | 433/29 |
| 5,267,857 | 12/1993 | Sickler | 433/29 |
| 5,538,423 | 7/1996 | Coss et al. | 433/98 |

*Primary Examiner*—Cary E. O'Connor
*Attorney, Agent, or Firm*—Oblon, Spivak, McClelland, Maier & Neustadt, P.C.

[57] ABSTRACT

An illumination system for use in combination with a fluid-driven, fiber optic dental handpiece having a proximal end with a light transmitting fiber optic rod and a plurality of fluid transmitting conduits extending therefrom in standardized configuration. The illumination system includes a control unit for supplying a regulated source of electric power, a air/water supply tube including a pair of electrical wires connected to the control unit for supplying fluid and electric power to the dental handpiece. Also included is a connector assembly for releaseably connecting the supply tube to the dental handpiece. The connector assembly includes a connector unit in the form of a generally cylindrical block of conductive material, preferably aluminum, which has a plurality of longitudinally oriented fluid transmitting channels extending therethrough and an axially aligned socket disposed along an outer periphery thereof which socket is sized for receiving a replaceable miniature halogen light bulb assembly. The connector unit body functions as a grounded electrical connection and a heat sink for the light bulb assembly. The connector unit is contained within an outer cylindrical strain relief shield housing. An improved quick-disconnect fluid tight coupling including a rotatable latch ring is provided for fastening the strain relief shield housing and connector unit to the proximal end of the dental handpiece upon a ¼ turn rotation of the latch ring.

4 Claims, 4 Drawing Sheets

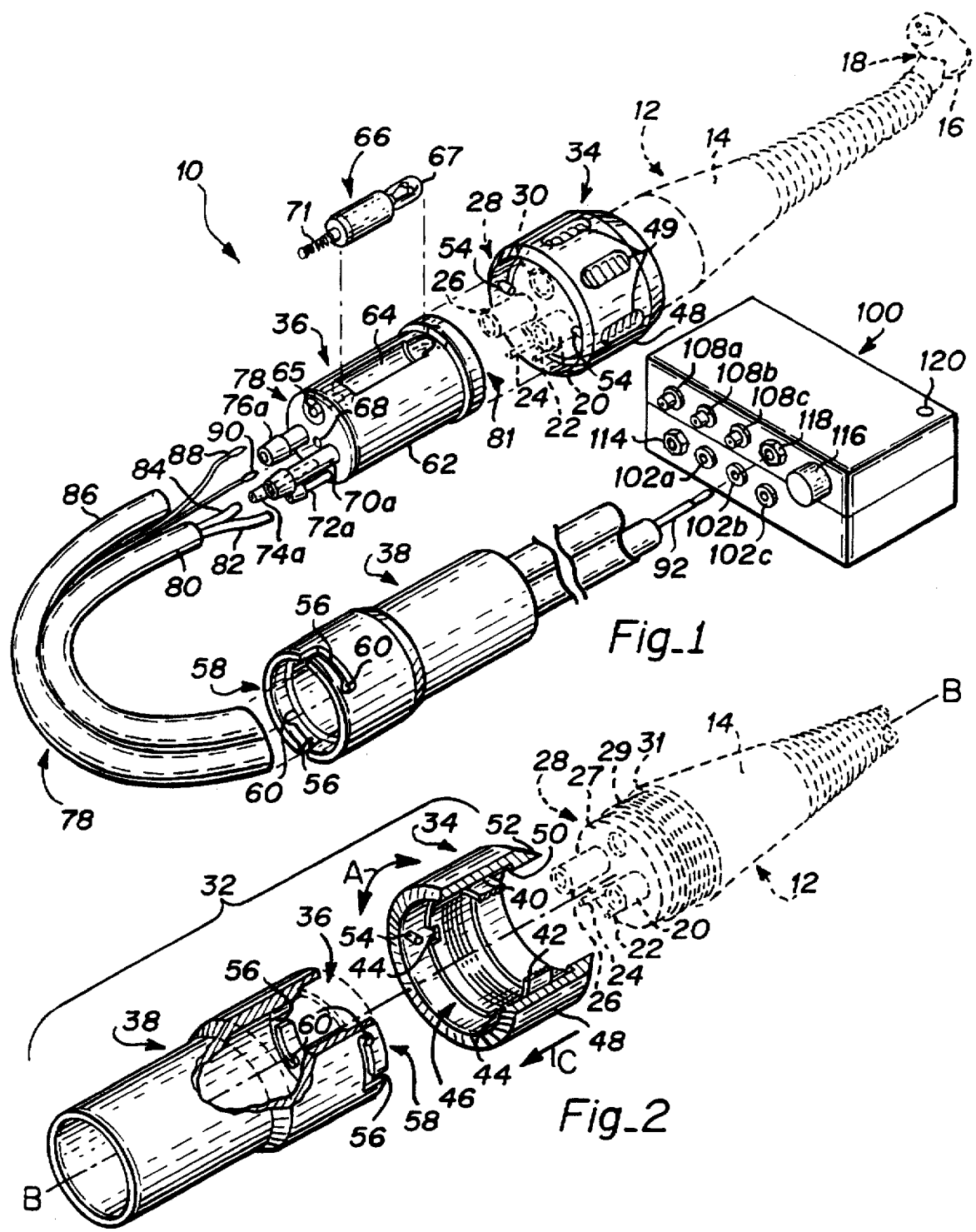
Fig_1
Fig_2

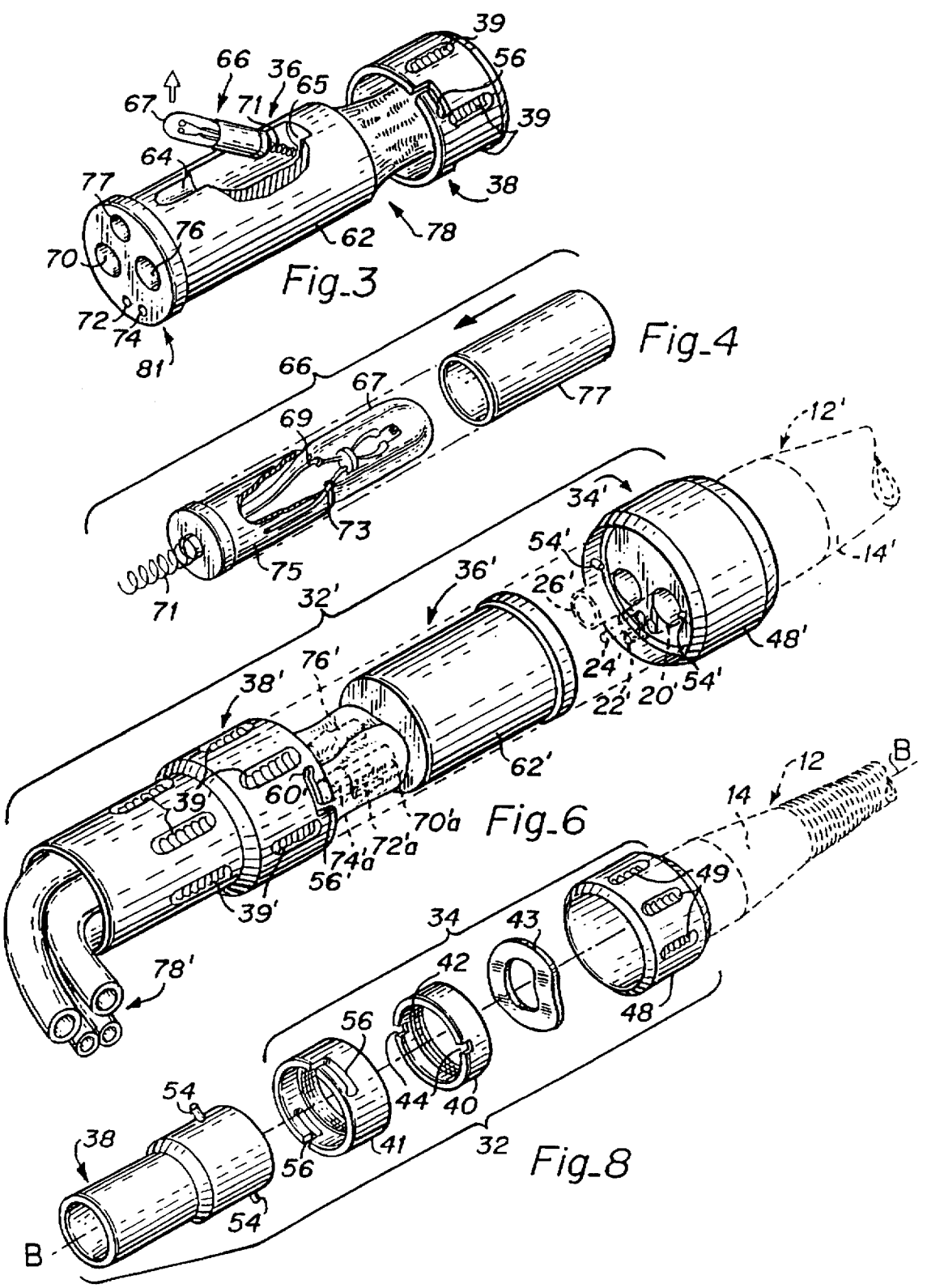

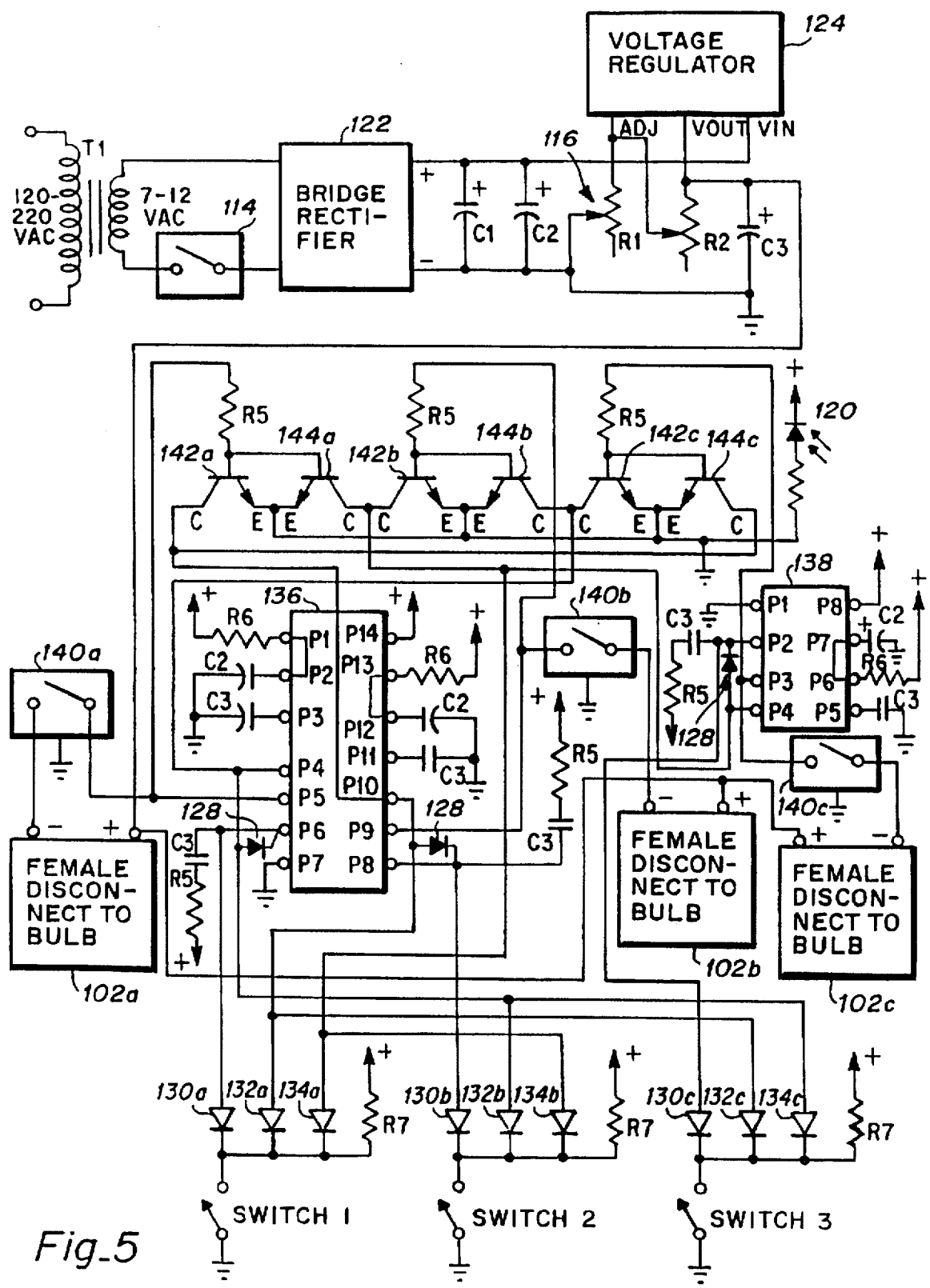
Fig_5

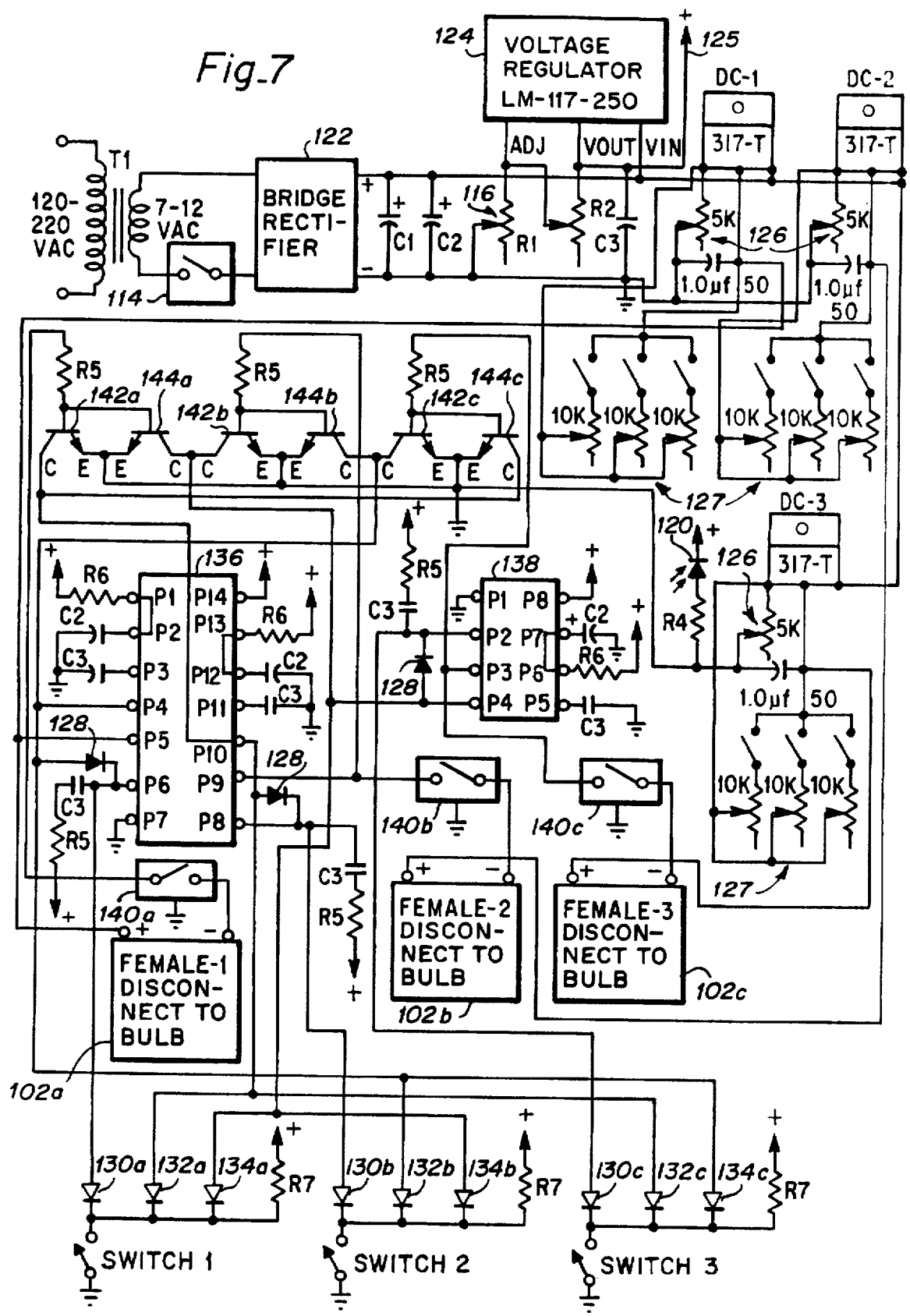

ILLUMINATION AND CONNECTOR DENTAL HANDPIECE ASSEMBLY

CROSS-REFERENCE TO RELATED APPLICATIONS

This is a National Phase divisional application of PCT/US94/12520 filed Nov. 3, 1994, published May 11, 1995 as WO95/12360, which in turn is a CIP of U.S. Pat. No. 5,476,379 issued Dec. 19, 1995 from U.S. Ser. No. 147,750 filed Nov. 4, 1993, priority as to which is claimed under 35 U.S.C. §§120 and 365 (c).

BACKGROUND

Connector assemblies which include means for receiving a miniature quartz halogen or similar light bulb in order to provide a light source for a fiber optic equipped dental handpiece are well known from the prior art. It is also well recognized that in order to achieve the necessary brightness for the job at hand, the quartz halogen bulbs must operate at a high burning temperature, preferably in the range of 2500°–2900° F. However, such high operating temperatures generate an excessive amount of radiant heat which result in the dental handpiece and connector becoming uncomfortable to handle for prolonged periods of use.

U.S. Pat. No. 4,334,863 issued to Magid et al. discloses a three element dental handpiece illuminator system which attempts to balance the above described brightness and overheating problem associated with use of a quartz halogen bulb. The illuminator system includes: (1) a replaceable plug-in cartridge having a small quartz halogen lamp enclosed therein; (2) an adaptor unit disposed permanently connected to the air/water/power supply hose; and (3) a cylindrical outer shield member which encloses both the adaptor and plug-in cartridge and couples the entire three element illuminator system to the threaded end of the dental handpiece connector. Both the adaptor and plug-in cartridge have a plurality of longitudinally oriented fluid transmitting channels or conduits which correspond in configuration to the fluid conduits of the dental handpiece. The quartz halogen bulb of Magid is permanently mounted within an internal axially aligned socket of the plug-in cartridge.

Magid teaches to prevent excess temperature rise of the illuminator in two ways. First, there is provided an air space between the bulb and its surrounding socket wall and second, there is an air space provided between the outer peripheral surface of the plug-in cartridge and the surrounding cylindrical housing. The two air spaces absorb the radiant heat transfer from the bulb to the plug-in cylindrical housing, respectively. Magid also teaches that this radiant heat absorbed by the air space is cooled or carried away by the continuous flow of air and water through the fluid conduits of the plug-in cartridge. In other words, Magid suggests to maintain the temperature of the illuminator at a tolerable level by convection heat transfer wherein the air heated by the halogen bulb is carried off by the drive air, exhaust air, and/or water coolant which are continuously transmitted through the illuminator during use of the dental handpiece.

In a commercial embodiment of the illuminator constructed in accordance with the Magid patent, the socket for the bulb is in direct air communication with the drive air and exhaust air conduits of the plug-in unit. This is done presumably to set up the desired connection heat transfer to maintain the outside surface temperature of the connector at or below a predetermined a tolerable level. In order to replace the halogen bulb, the entire plug-in cartridge is removed and discarded in favor of a new plug-in cartridge with enclosed bulb. This requires the user to repeatedly break the air/water and electrical connections between the plug-in cartridge and the adapter interface. Over time, the repeated disconnections tend to cause leaks in the adjacent gasket seal, and as a result, corrosion of the electrical connections in this region is likely to occur. This arrangement also adversely affects the operating life of the bulb, since the lubricants present in the turbine head of the dental handpiece eventually find their way into the exhaust air stream, and this results and coats the bulb. This, in turn, leads to premature dismiss and eventual failure of the bulb.

U.S. Pat. No. 4,330,274 issued to Friedman et al. discloses a dental handpiece illuminator system which is similar in design in the Magid system in that it also includes a generally cylindrical connector unit having a socket for containing a halogen bulb and an outer cylindrical shield member for enclosing the connector unit. Also, like the Magid design, the shield member of Friedman includes threats disposed along an inner surface at one end for threaded engagement with the external threads of the dental handpiece. The connector unit includes a spring-loaded bulb socket for convenient bulb replacement. Friedman teaches to permanently secure one end of the connector unit to the air/water and electronic power supply tubing in order to overcome the problems of leaky seals and corrosion of adjacent electrical contacts caused by the required repeated disconnection of a plug-in type cartridge unit from the air/water and electrical supply tubing of other prior art designs.

In both the dental handpiece illuminator system of Magid and Friedman, the user must unscrew the outer shield member from the handpiece to get at the connector unit or plug-in cartridge to replace a burned out light bulb. The time required to replace a bulb in these systems may be unacceptably long and therefore may discourage some dentists from continuing to use such an illumination system. While quick disconnect assemblies for dental handpiece connectors are generally known in the art, these prior art quick disconnect assemblies use a centered axial plug-type connection, similar in design to a common high pressure air hose. However, in view of the many design difficulties associated with the proper alignment and isolation of the optical pathway and light bulb socket with respect to the fluid transmitting channels of the connector unit, such central, axial plug-type quick disconnect coupling assemblies have not yet been successfully implemented in a conventional illuminated connector assembly for fluid driven, fiber optic dental handpieces.

THE INVENTION

SUMMARY

Accordingly, it is a primary objective of the present invention to provide an illumination system and connector assembly for a dental handpiece system which overcomes the problems of the prior art designs using quartz halogen type light bulb assemblies.

The invention includes an improved three element connector assembly combination for coupling a fluid driven, fiber optic equipped dental handpiece to a fluid supply tube. The connector assembly includes a connector unit formed as a generally elongated cylindrical block of material, preferably of a thermally conductive material such as for example, aluminum. The connector unit includes an axially aligned socket disposed along an outer periphery thereof which is sized for receiving a replaceable halogen (preferably krypton) light bulb assembly. The connector unit also includes a plurality of fluid conduits configured to match the standardized fluid conduit configuration of the dental handpiece connector end. The connector assembly also includes a cylindrical strain relief shield housing for enclosing the connector unit and a coupling assembly which provides for quick-disconnect, fluid tight attachment of the outer strain relief shield and enclosed connector unit to the dental handpiece.

The coupling assembly comprises a rotatable latch ring and threaded retainer ring which attaches to the threaded proximal end of the dental handpiece unit. The latch ring includes a pair of diametrically opposed and radially inwardly directed pins which are operative to positively lockingly engage a pair of receiving slots formed on the corresponding end of the cylindrical outer shield housing in a bayonet-type fashion, thereby bringing the cylindrical strain relief shield and connector unit contained therein into fluid tight contact with the receiving end of the dental handpiece unit. The rotatable latch ring coupling described above permits for rapid connection and disconnection upon only about ¼ turn rotation of the latch ring. This provides a significant time advantage over the threaded connection scheme used for joining the strain relief shield to the threaded end of the dental handpiece of the prior art designs.

The preferred light bulb assembly uses a krypton halogen bulb which provides a noticeably brighter and clearer light than the conventional quartz halogen bulb used in the prior art illumination systems. The krypton bulb, however, also operates at a higher burning temperature, typically around 3,050° F. which, in turn, generates a greater amount of radiant heat which must be evenly dissipated so that the dental handpiece and connector assembly never become too hot to handle over prolonged periods of time. To overcome this problem, the light bulb assembly is disposed in direct contact with the surrounding socket wall in the connector body such that the connector body forms a thermal heat sink for the high temperature burning bulb. This heat is then evenly distributed to the surrounding cylindrical shield and dental handpiece unit. The outer cylindrical strain relief shield is also preferably formed from a thermally conductive material such as, for example, stainless steel.

The illumination system also includes improved circuity for the controlled illumination of a plurality of dental handpiece units. In a preferred embodiment, a controlled unit is provided with air switch inputs for three separate dental handpiece units each having illumination capability.

The improved connector assembly of the present invention may also be used in combination with non-illuminated dental handpieces without modification. Alternatively, a second embodiment for a dental handpiece connector is disclosed wherein the socket for receiving the light bulb assembly is omitted.

Other features and objects of the present invention will become apparent from the following written description, drawings and appended claims.

DRAWINGS

FIG. 1 is an isometric view of one embodiment of the dental handpiece connector assembly and illumination system of the present invention adapted for use with a dental handpiece having a fiber optic light transmitting tube (dental handpiece shown in phantom);

FIG. 2 is an enlarged exploded isometric view of the connector assembly of FIG. 1;

FIG. 3 is an enlarged isometric 180° reverse angle view of the light bulb equipped connector unit of FIGS. 1–2. FIG. 3 shows an array of fluid conduits configured for an ISO standard high-speed handpiece configuration disposed at the distal end of the connector unit;

FIG. 4 is an enlarged exploded isometric view showing the detail of the light bulb assembly;

FIG. 5 is a schematic circuit diagram of the lighting system control of the present invention;

FIG. 6 is an isometric view of a second embodiment of the dental handpiece connector assembly of the present invention for use with a non-illuminated standard ISO configuration dental handpiece (shown in phantom);

FIG. 7 is a schematic circuit diagram of a second embodiment of the lighting system control of the present invention; and FIG. 8 is an isometric view of an alternate embodiment of the connector assembly of the present invention.

DETAILED DESCRIPTION OF THE BEST MODE

The following detailed description illustrates the invention by way of example, not by way of limitation of the principles of the invention. This description will clearly enable one skilled in the art to make and use the invention, and describes several embodiments, adaptations, variations, alternatives and uses of the invention, including what I presently believe is the best mode of carrying out the invention.

A dental handpiece illumination system constructed in accordance with one embodiment of the present invention is shown in FIG. 1, and is designated generally by reference number 10. The dental handpiece illumination system 10 is preferably used in combination with a standard dental handpiece 12 (shown in phantom) having a body 14 a turbine head 16 disposed at a distal end 18 of the body 14 and a plurality of fluid transmitting conduits 20, 22, 24 and 26 which extend from a second or proximal end 28 of the body 14. The proximal end 28 further includes a light transmitting fiber optic rod 30 for providing a beam of light projecting from the turbine head 18.

The arrangement of the fluid conduits 20, 24, 26, 28 and the fiber optic rod 30 are representative of an ISO standardized configuration for a high speed dental handpiece wherein conduit 20 carries drive air, conduit 22 carries water coolant, conduit 24 carries chip air or air coolant and conduit 26 carries exhaust air.

With reference now to FIGS. 1 and 2, the dental handpiece illumination system 20 comprises a connector assembly 32, a supply hose 78 and a control system 100.

The connector assembly 32 includes a coupling assembly 34, a connector unit 35 and a cylindrical strain relief shield 38. In use, the coupling assembly 34 couples the strain relief shield 38 and enclosed connector unit 36 to the proximal end 28 of the dental handpiece 12.

The coupling assembly 34 further includes a retainer ring 40 having interior threads 42 which engage the exposed external threads 29 of the proximal end 28 of the dental handpiece body 14. The retainer ring 40 is also provided with a plurality of notched recesses 44 disposed at spaced intervals along a periphery of a proximal end 46 thereof. The notched recesses 44 are adapted for receivingly engaging the pronged end of an installation tool (not shown) used for screwing the retainer ring 40 onto the external threads 29 of the dental handpiece 12. An installation tool may, for example, simply comprise a pair of needlenose pliers.

An outer latch ring 48 is also provided and surrounds the retainer ring 40 in concentric fashion. In this way, the retainer ring 40 serves as a bushing for the latch ring 48 and permits the latch ring 48 to rotate about a common longitudinal center axis B—B in the direction as shown by double-ended arrow A. The latch ring 48 is also permitted to move back and forth in the axial direction with respect to the retainer ring as shown by double ended direction arrow C. The axial movement of the latch ring 48 is constrained at one end by the contact of interior shoulder 50 of the latch ring 48 and the adjacent edge of the retainer ring 40 and is constrained at the other end by the contact of edge 52 of the latch ring 48 with shoulder 31 of the dental handpiece 12.

The latch ring 48 includes a pair of diametrically opposed pins 54 which, in use, are receivingly engabable within corresponding receiving slots 56 of the adjacent free end 58 of the cylindrical strain relief shield 38. To complete a coupling, the pins 54 of latch ring 48 are inserted within the corresponding receiving slots 56 of strain relief shield 38 whereby the latch ring 48 is then rotated about ¼ turn in the counterclockwise direction until the pins 54 click into positive locking engagement within the corresponding end detents 60 of the receiving slots 56. This positive twist lock action compresses the gasket seal 27 disposed between the dental handpiece proximal end 28 and the connector unit distal end 81 thereby providing a fluid tight connection. The latch ring 48 is preferably provided with a plurality of spaced longitudinally oriented flutes 49 to facilitate grip handling by a user when rotated for coupling/uncoupling operation.

The connector unit 36 preferably comprises an elongated cylindrical block of thermally conductive material, preferably aluminum. The block has a plurality of fluid transmitting channels or conduits 70, 72, 74 and 76 (see FIG. 3) arranged in configuration for communication with the respective fluid transmitting conduits 20, 22, 24, 26 of the dental handpiece 12. As best seen in FIG. 1, a plurality of barb ferrules 70a, 72a, 74a and 76a corresponding to the respective fluid transmitting conduits 70, 72, 74 and 76 of the connector unit 36 are shown extending from the proximal end 78 of the connector unit 36. The barb ferrules 70a, 72a, 74a and 76a are adapted to be fixedly connected to their corresponding air and water conduits 80, 82, 84 and 86 of the supply hose 78. The barb ferrules are preferably staggered in length with respect to one another. Staggering the barb ferrules in this manner facilitates the initial connection of the supply hose 78 to the proximal end 78 of the connector unit 36 and also minimizes swelling of the resulting tubing connection thereby permitting the strain relief shield 38 to be unobstructively moved over this connection when access to the connector unit 36 is desired.

The connector unit 36 further includes a socket 64 for receiving a light bulb assembly 66 therewithin. The socket 64 forms an opening 77 at the distal end 81 of the connector unit 36 adapted to receive the fiber optic rod 30 of the dental handpiece 12 (see FIG. 1). At the base end of the socket 64 there is disposed a shielded plug-in connector 65 which is electrically connected to electrical wire 88 of the supply hose 78 and includes a bore hole (not shown) for receiving the spring end of the light bulb assembly 66. A second electrical wire 90 of the supply hose is grounded to the connector body 62 by crimp or solder connection within hole 68 of the connector body 62. The connection scheme for the light bulb assembly is described in more detail below with reference to FIG. 4.

The control system 100 supplies power to the electrical wires 88 and 90 of the supply hose 70. The preferred control system 100 shown in FIGS. 1, 5 and 7 is capable of providing illumination control for three separate dental handpieces and includes three female electrical disconnects 102a, 102b and 102c for receiving the respective male electrical jack input associated with each supply hose. As seen in FIG. 1, the electrical jack input 92 (corresponding to wires 88, 90 of the supply hose 78) is shown directed towards insertion within the middle electrical disconnect 102b. Associated with each electrical disconnect 102a, 102b and 102c are air pressure switches (handpiece selectors) 108a, 108b and 108c, respectively, which activate the respective air line for each dental handpiece. The air and water conduits of the supply hose are connected to a provided conventional air/water supply sources (not shown). A master air input switch 114 is also provided and is connected by a T-connector (not shown) to each of the air pressure switches 108a, 108b and 108c and to a master air pressure control switch associated with the provided dental unit (not shown). The control system 100 further includes an intensity know 116 for regulating the brightness of the light bulb assembly 66 and an AC adaptor input jack 118. Also shown is an LED 120 which is illuminated when the master air switch 114 is activated to the "on" position.

FIG. 3 shows a 180° reverse angle isometric view of the connector unit 36 wherein the block 62 is partially cut away to illustrate the spring-loaded electrical connection of the light bulb assembly 66 within the shielded plug-in connector 65 disposed at the base end of the socket 64. Also clearly visible in FIG. 3 are the fluid transmitting channels 70, 72, 74 and 76 and the hole 77 which are arranged in standard configuration at the distal end 81 of the connector unit 36 for engagement with the respective fluid transmitting conduits 20, 22, 24, 26 and fiber optic rod 30 of the dental handpiece proximal end 28.

An optional feature is the provision of a plurality of spaced longitudinally oriented flutes 39 (FIG. 6) along the periphery of the strain relief shield 38 to facilitate grip handling by a user when coupling the latch ring 48 to the strain relief shield 38. These flutes 39 may be similar in size and shape to the flutes 49 of the latch ring 48 (see FIG. 1).

FIG. 4 shows an exploded isometric view of the light bulb assembly 66. The light bulb assembly 66 preferably comprises a krypton halogen envelope 67 including a first wire filament 69 electrically connected to a metal spring member 71 and a second ground wire filament 73 directed along the outside of the envelope and over an insulator 75 surrounding a base end of the envelope 67. A metal sleeve 77 is fitted over the envelope 67 and insulator 75 such that it directly contacts the second filament 73. The socket 64 is sized sufficiently small in diameter such that it makes direct contact with the metal sleeve 77. Thus, the second wire filament 73 is grounded to the aluminum connector body 62 of the connector unit 36, which, in turn is connected to the electrical wire 90 of the supply hose 78 at crimp fitting 68. The electrical circuit for the light bulb assembly 66 is completed by the inserted connection of metal spring 71 within receiving borehole of the shielded plug-in connector 65 disposed at the base end of socket 64.

The above-described arrangement provides a simplified spring-loaded bulb assembly 66 within the connector unit 36. Further, the body 62 of the connector unit 36, which preferably comprises a thermally and electrically conductive material such as aluminum, provides an efficient heat sink for evenly distributing and dissipating the excess heat generated by the krypton halogen bulb to the surrounding strain relief shield 38 and dental handpiece 12. In this way, the bulb is permitted to run at a desired high temperature sufficient for optimum efficiency and brightness without causing isolated hot spots on the outer connector housing. The light bulb assembly 66 may be quickly ejected from the socket 64 by using a pointed instrument such as a pen tip or fingernail, for example, to push down on the bulb assembly 66 and compress spring 71 so that the bulb assembly 66 may be ejected out of the socket 64.

The control system for supplying power to the electrical wires 88 and 90 of the supply hose 78 for energizing the light bulb assembly 66 is shown in FIG. 5 and 7. FIG. 5 has a fixed voltage regulator to provide a common voltage output to each of the disconnects 102a, b, and c, while 7–12V goes directly to the board without regulation (i.e., fixed voltage). FIG. 7 is a second embodiment in which the output to each handpiece via the disconnects 102a, b, c may be adjusted and preset by the adjustable voltage regulators DC1, DC2 and DC3. In addition, regulator 124 permits setting the voltage to the board.

The preferred control circuit of the present invention comprises many commercially available high speed CMOS parts. Accordingly, for convenience in the description of the preferred embodiment these components will be referenced by their model number and manufacturer where appropriate.

Common to both embodiments of FIGS. 5 and 7, power may be provided from any conventional source of alternating line voltage through an appropriate step down transformer T1. In the example shown, from 120–220 volts AC is dropped to 7–12 volts AC through transformer T1. The 7–12 volt output across the secondary winding of transformer T1 is rectified to a DC source of power by the bridge rectifier 122 upon actuation of the master air pressure switch 114. Capacitors C1 and C2 act as filters to reduce spikes and ripple in the AC wave form. The full wave rectified output $V_{in}$ from the bridge rectifier 122 is applied to a conventional voltage regulator circuit 124 such as, for example, any one of LM117 to LM250 from National Semiconductor Corporation of Santa Clara, Calif. R1 bulb which is activated by the intensity knob 116 of the control system 100 (see FIG. 1).

In FIG. 5 the regulated output $V_{out}$ of the voltage regulator 124 is applied to the positive input of the respective female electrical disconnects 120a, 102b, 102c for selectively illuminating the light bulb assembly associated with each handpiece. The nonregulated output from the voltage regulator 124 powers the LED 120 as well as the other electrical components of the circuit in a conventional manner as indicated by the positive (+) arrow associated with each powered component. In FIG. 7 the $V_{out}$ from regulator 124 controls the board only (see + arrow 125) whereas DC1, 2 and 3 independently control the bulb intensity of three individual handpieces. Thus the voltage is capable of being individually preset and the brightness controlled. The limit potentiometers 128 in DC 1, 2 and 3 are adjustable from about 1.2 to 10V, permitting voltage to the lamp to be set to the individual bulb voltage requirement for a given handpiece, while thereafter the intensity is controlled via potentiometer 126. For example, 128 can be set for 3.25 V for Aerostar Dental and Kinetics, 5.5V for Star and Lares, and 9V for other types. By making $V_{in}$ adjustable, the circuit has highside limits to the bulb voltage.

Common to both embodiments, the three female electrical disconnects 102a, 102b and 102c each represent a connection for an individual dental handpiece which may be controlled by the control system 100 of the present invention. The following description will describe the operation of a first dental handpiece associated with SWITCH 1 in combination with its corresponding circuit components. The control system uses common voltage and independent circuitry for each of the three SWITCHES 1, 2, 3. For ease in understanding the circuit diagrams of FIGS. 5 and 7, the reference numerals for the circuit components associated with SWITCH 1 are designated by an "a" following each reference number, e.g., air pressure input switch 108a is associated with SWITCH 1. Similarly, common circuit components for SWITCH 2 and SWITCH 3 are designated by a "b" and "c" following their respective reference numerals. SWITCH 1 (as well as SWITCH 2 and SWITCH 3) represents a single throw, momentary push button switch.

As a user removes the first dental handpiece from its holder on the master unit (not shown) and steps on the air pressure foot control associated therewith (also not shown), air pressure is provided to drive the handpiece and accordingly closes SWITCH 1. This causes a low signal to form at the output of diode 130a which is applied to the trigger P6 of a conventional dual timing circuit 136 associated with both SWITCHES 1 and 2 such as, for example, a LM556 Dual Timer from National Semiconductor. The two timer portions of Dual Timer 136 operate independently of each other and share only $V_{cc}$ and ground. The first timer portion comprises pins P1–P7 and is dedicated to SWITCH 1. The second timer portion comprises pins P8–P14 and is dedicated to SWITCH 2. A third Timer 138, preferably a LM555 Timer also from National Semiconductor, is dedicated to SWITCH 3.

Simultaneous with the activation of trigger pin P6, a low signal is also formed at the outputs of diodes 132a and 134a which causes a low signal to be applied to reset pin P10 of Dual Timer 136 (i.e., the SWITCH 2 portion) and reset pin P4 of Timer 138 (SWITCH 3). The low signal at the trigger pin P6 causes the output at P5 to go from low to high which, in turn, closes MOSFET 140a. This provides a negative signal to the female disconnect 102a and completes the circuit and cause the light bulb for the first dental handpiece to turn on. Switch 140a is preferably a high speed MOSFET ECG-66 from Phillips ECG Incorporated or IRF510-512 from RCA. Diodes 128 signal the timer chip reset.

The output at pin P5 of the Dual Timer 136 is also directed through a 10k resistor, R5, and is applied to a pair of conventional medium power signal transistors, 142a and 144a, for example a medium power device, such as a PN2222 from National Semiconductor. The low state output from transistor 142a is then applied to the reset pin P10 to suppress the SWITCH 2 portion of Dual Timer 136. Similarly, a low signal is passed through the second transistor 144a and is applied at the reset pin P4 of Timer 138 to suppress the timing circuit for SWITCH 3. In other words, as long as the trigger P6 associated with the SWITCH 1 portion of Dual Timer 136 is activated, the SWITCH 2 portion of Dual Timer 136 and the Timer 138 are locked into a low state so they cannot false trigger.

Then SWITCH 1 is open, i.e., where the user removes foot pressure from the foot operated pressure switch (not shown), the SWITCH 1 portion of the Dual Timer 136 for the female disconnect 102a remains closed for a predetermined delay period, preferably on the order of 10 seconds or so to continue the supply of power to the light bulb of the dental handpiece independently of the air operation of the handpiece drill for the duration of the delay period. If, however, the user wishes to immediately pick up and use a second dental handpiece, the closure of its respective air switch, for example SWITCH 2, causes a low signal to form at the output of diodes 130b, 132b and 134b. This, in turn, triggers pin P8 of the Dual Timer 136 (i.e., that portion of the Dual Timer dedicated to SWITCH 2) and suppresses the other Timers by sending a low signal to the reset pin P4 of Dual Timer 136 (SWITCH 1) and the reset pin P4 of Timer 138 (SWITCH 3). A low signal at trigger P8 of the Dual Timer 136 generates a high signal at P9 which is applied to the switch 104b. This, in turn, completes the circuit for the female disconnect 102b and lights the bulb for the second dental handpiece. At the same time the high output from Pin P9 is stepped down through the R5 resistor and is converted to a low signal at the output of transistors 142b, 144b which is applied to the reset pin P4 of Dual Timer 136 (i.e., the SWITCH 1 portion) and reset Pin P4 of Timer 138 (SWITCH 3). The operation of SWITCH 3 is similar to the above described function of the timing circuit for SWITCHES 1 and 2. For fiberoptic control of the power supply, bridge rectifier and mosfets should be increased in size (values) accordingly.

Shown in FIG. 6 is an alternative embodiment of the invention, which is of somewhat simplified and more compact construction. For each of description, parts of this embodiment which correspond to parts of the first preferred embodiment are identified by corresponding primed reference numerals, and only the significant differences are described in detail.

More particularly, the alternate embodiment for the connector assembly 32' omits a socket for housing a light bulb assembly. In other words, the connector assembly 32' comprises simply of a coupling assembly 34', a connector unit 36' and a strain relief shield 38'. The connector unit 36' contains a plurality of longitudinally oriented fluid transmitting channels therein which correspond in both size and number to a particular fluid conduit configuration for the dental handpiece for which it is to be attached. For example, in the alternate embodiment shown in FIG. 6, the coupling assembly 32' is intended for use with a high speed dental handpiece having four fluid transmitting conduits. However, it is understood that the coupling assembly 32' of the present invention can be designed with any fewer or greater number of fluid transmitting channels for connection with any one of a number of standard types of fluid driven dental handpieces.

FIG. 8 shows another embodiment of the bayonet quick connect/disconnect connector assembly 32 of this invention in which the coupling assembly 34 is mounted on the handpiece, and comprises the rotatable latch ring 48, a spring washer 43 and retainer ring 40 as above described for the FIGS. 1, 2 and 6 embodiment, but wherein the bayonet pins 54 are mounted on the strain relief shield 38. These pins are received in bayonet slots 56 in a bayonet ring that is swaged (or heat pressed) into the rotating latch ring 48. The notches 44 in retainer ring permit mounting on the handpiece body 12 via threads 42 as before. Likewise, the spring 43 axially biases the assembly to insure retention of the pins 54 in the detents of slots 56 as before. The gasket seal 27, connector unit 36, tubing assembly 28 and flutes 38 are not shown.

It should be understood that various modifications within the scope of this invention can be made by one of ordinary skill in the art without departing from the spirit thereof. I therefore wish my invention to be defined by the scope of the appended claims as broadly as the prior art will permit, and in view of the specification if need be.

I claim:

1. A universal control circuit for an illumination system for use in connection with a dental delivery system having a plurality of a fluid-driven fiber optic dental handpieces, each of which has a body with a proximate end, a light transmitting fiber optic rod disposed in said body and a plurality of fluid transmitting conducts extending therefrom in standard configuration, and a connector assembly including a light bulb providing illumination to a work area via said fiber optic rod, comprising in operative combination:

a) at least one voltage regulator providing power from its positive side to said bulb;

b) a variable feedback resistor setting highside current connected to said voltage regulator so that as voltage to said bulb is adjusted, the current and voltage are adjustably controlled for use with all types of handpiece illumination bulbs.

2. A universal circuit as in claim 1 which includes:

a) means for delaying cutoff of power to said bulb when said handpiece is deactivated so that the user may illuminate the work area without handpiece burr operation during said delay period, and restart said handpiece before the end of said delay without interruption in illumination.

3. A universal circuit as in claim 2 which includes:

a) a plurality of switches, each one keyed to a different one of plural handpieces connected so that upon activating a second handpiece, the delay for all other handpieces is locked out.

4. A universal circuit as in claim 1 which includes:

a) a plurality of voltage regulators, one of which is dedicated to power the circuit, and one each for powering the bulb of each handpiece;

b) each of said bulb voltage regulators is associated with switch means for independently selecting voltage and current for each handpiece individually; and c) means for individually controlling intensity of illumination of each of said handpiece bulbs by control of the voltage.

* * * * *